United States Patent [19]

Maurer et al.

[11] Patent Number: 4,522,748
[45] Date of Patent: Jun. 11, 1985

[54] BICYCLIC ALDEHYDE AND ITS USE AS PERFUMING AGENT

[75] Inventors: Bruno Maurer, Collonges-Bellerive; Arnold Hauser, Aire-la-Ville, both of Switzerland

[73] Assignee: Firmenich SA, Geneva, Switzerland

[21] Appl. No.: 524,574

[22] Filed: Aug. 19, 1983

[30] Foreign Application Priority Data

Sep. 6, 1982 [CH] Switzerland .......................... 5280/82

[51] Int. Cl.³ .................... C07C 47/115; A61K 7/46
[52] U.S. Cl. ............................. 252/522 R; 568/445; 426/538
[58] Field of Search ..................... 568/445; 252/522 R

[56] References Cited

U.S. PATENT DOCUMENTS 4,270,007  5/1981  Hagen et al. .................... 568/445

OTHER PUBLICATIONS

Fieser et al., Reagents for Organic Synthesis, vol. 8, (1980), 198.
House, Modern Synthetic Reactions, 2nd Ed., (1972), 319.

Primary Examiner—Bernard Helfin
Attorney, Agent, or Firm—Pennie & Edmonds

[57] ABSTRACT

Bicyclic aldehydes of formula

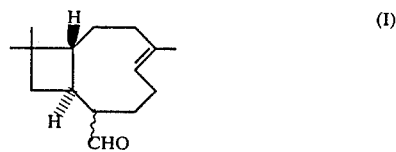

possess useful organoleptic properties and can be used advantageously as perfume and flavor ingredients. Compounds (I) develop woody and ambery odor notes and woody, musky and earthy gustative characteristics. They are prepared by a multistep process starting from (E)-13-norcaryophyll-4-en-8-one.

2 Claims, No Drawings

BICYCLIC ALDEHYDE AND ITS USE AS PERFUMING AGENT

BRIEF SUMMARY OF THE INVENTION

The present invention relates to the field of perfumery and flavors. In particular, it provides novel bicyclic aldehydes of formula

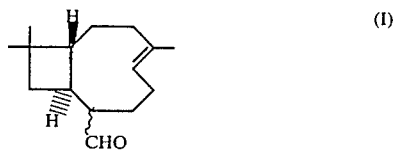

wherein  indicates a C—C single bond of cis or trans configuration with respect to the neighbouring C  H bond.

The invention provides further a perfume or flavoring composition containing as organoleptically active ingredient a bicyclic aldehyde of formula (I).

Another object of this invention is a process for the preparation of bicyclic aldehydes (I) which process consists in the following consecutive steps:

a. reacting (E)-13-norcaryophyll-4-en-8-one with trimethylsulfonium iodide in the presence of a strong base to give the epoxide of formula

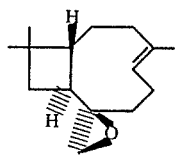

and b. reacting said epoxide with a Lewis-type acid and, optionally, separating the different constituents of the obtained isomeric mixtures by means of vapor phase chromatography.

THE INVENTION

Bicyclic aldehydes of formula (I) are novel compounds which may occur in different epimeric forms, viz. the isomers of formula

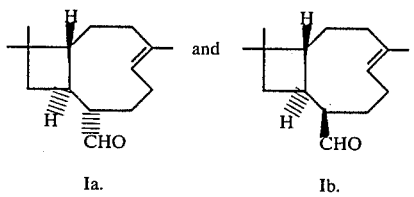

Ia.                     Ib.

They possess an original fragrance character. They develop in fact a smell reminiscent of freshly cut wood accompanied by a woody slightly camphory note. This character is usually found in costly natural amber or in decaline derivatives of the ambrinol type.

The dominating woody character is also accomplished by an aldehydic note, namely of the type found in some fatty aldehydes. Compounds (I) are thus eligible for a broad range of applications. They can be utilized both in alcoholic and in technical perfumery, for instance for the perfuming of soaps, cosmetics, shampoos, detergents, either in liquid or in solid form, fabric softeners, deodorizers, air-fresheners or waxes.

The proportions at which they can achieve the desired results vary in a wide range of values.

Those expert in the field know by experience that these values depend on the specific effect it is desired to achieve and on the nature of the thus perfumed material as well as on the nature of the coingredients in a given composition. Preferred concentrations are in the range of about 2 to 10% by weight, based on the total weight of the composition into which they are added. As usual, concentrations lower than the said given values, e.g. of the order of 0.5-1%, are deemed sufficient in the manufacture of perfumed articles such as soaps and detergents. Of course, concentrations higher than the above upper limits are used whenever perfume concentrates or "coeurs" are desired.

Compounds (I) also possess useful gustative properties and consequently they can be used for the aromatization of foodstuffs, beverages, pharmaceutical preparations and tobacco where they develop woody, musky and earthy notes. Such aromatic characters are developed at concentrations of about 1 to 100 ppm (parts per million) by weight based on the total weight of the flavored material. Owing to its typical gustative characters, compounds (I) find a utility in the aromatization of tobacco or tabacco products or to enhance the typical musky character of certain fruit, especially berries. As disclosed above, compounds (I) are prepared by a new process which utilizes a norcaryophyllenone as starting material. The process is illustrated by the following reaction pathway:

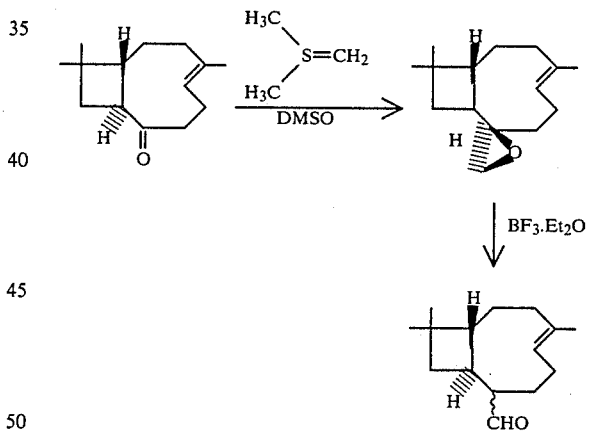

DMSO = dimethylsulfoxide (E)-13-Norcaryophyll-4-en-8-one, used as starting material in the said process, can be obtained in accordance with the method described in Helv. Chim. Acta 59, 1803 (1976).

The method followed will be described in a more detailed manner by the following examples wherein the temperatures are indicated in degrees centigrade.

EXAMPLE 1

(E)-Caryophyll-4-en-13-al a. 1.02 G (33 mM) of a 80% suspension of sodium hydride in oil were placed in a reaction vessel equipped with a magnetic stirrer and washed twice with petrol ether. 40 Ml of dimethylsulfoxide where then added and the mixture was kept stirring for 15 min at room temperature. 6.73 G (33 mM) of trimethylsulfonium iodide were added to the cooled reaction mixture (10°–15°) followed, after 5 min, by a solution of 3.5 g (16.9 mM) of (E)-13-norcaryophyll-4-en-8-one in 10 ml of dimethylsulfoxide. The mixture was kept stirring overnight at room temperature whereupon it was poured onto a mixture of ice-water. By extraction with petrol ether, washing of the combined extracts, drying over $Na_2SO_4$ and evaporation, a residue was obtained which, upon distillation in a bulb apparatus (60°/6.65×10⁻¹ Pa), gave 2.6 g (69%) of (1R,4E,8R,9S)-8,13-epoxycaryophyll-4-ene.

MS: 220(<1); m/z: 41(100), 55(58), 79(52), 69(50), 91(47), 67(45), 81(43), 93(40), 119(35), 134(29), 107(29), 43(29);

NMR(360 MHz; $CDCl_3$): 0.92 and 0.94 (6H, 2s); 1.26–1.56 (4H, m); 1.63 (3H,) broad s); 1.68–2.20 (8H, m); 2.56 (2H, AB system: $J_{AB}=5$; $\delta_A=2.53$, $\delta_B=2.60$); 5.50 (1H, m)δppm;

IR (liq.): 3050 and 1675 cm⁻¹.

b. 1 Ml of borontrifluoroetherate was added at 0° to 2.3 g (10.5 mM) of a solution of the epoxide prepared according to letter a. above in 10 ml of ether, whereupon the reaction mixture was stirred at 0° during 30 min and then poured onto ice and extracted with pentane. The extract was washed until neutrality with a saturated solution of sodium bicarbonate and water, dried over $Na_2SO_4$ and the solvent distilled.

The raw aldehyde obtained (2.1 g) was chromatographed over silica gel to give a fraction of 1.07 g (46%) of an epimeric mixture, which was then distilled by means of a bulb apparatus (90°/1.33×10⁻¹ Pa). The two isomers were then separated one from the other by vapor phase chromatography using a silicone oil column (200°).

Isomer A:

IR ($CHCl_3$): 3020, 2830, 2730, 1720 and 1675 cm⁻¹;

MS:M⁺=220(1.5); m/z: 135(100), 41(98), 79(67), 93(66), 67(55), 69(53), 81(52), 107(50), 55(49), 95(41), 91(36), 164(27);

NMR (360 MHz, $CDCl_3$): 0.99 (6H, s); 1.64 (3H, broad s); 5.26 (1H, m); 9.69 (1H, broad s)δppm;

Isomer B:

IR($CHCl_3$): 3020, 2830, 2730, 1720, 1675 cm⁻¹;

MS: M⁺=220(2); m/z: 135(100), 41(46), 79(33), 93(32), 69(27), 67(27), 81(24), 55(24), 107(22), 95(17); 91(15), 136(13);

NMR (360 MHz; $CDCl_3$): 0.95 and 0.96 (6H, 2s); 1.64 (3H, broad s); 2.43 (1H, m); 5.45 (1H, m); 9.35 (1H, d, J=4)δppm.

EXAMPLE 2

A perfume extract was prepared by mixing the following ingredients (parts by weight):

| | |
|---|---|
| Discolorized oak-moss absolute 10%* | 200 |
| Vetyveryl acetate | 100 |
| IRALIA ®⁽¹⁾⁽²⁾ | 80 |
| Lavender oil | 50 |
| Synth. jasmin absolute | 50 |
| CYCLOSIA ®⁽¹⁾⁽³⁾ | 40 |
| Undecylenic aldehyde 10%* | 40 |
| Decanal 10%* | 30 |
| Synth. lily-of-the-valley | 30 |
| Musk ketone | 30 |
| Synth. bergamot | 30 |
| Lemon oil | 20 |
| Neroli bigarade oil 50%* | 20 |
| Styrallyl acetate | 20 |
| Ethylvanilline 10%* | 20 |
| Synth. civet | 20 |
| Synth. ambra | 20 |
| Undecalactone 1%* | 20 |
| Nectarol⁽¹⁾ | 15 |
| δ-Decalactone 10%* | 15 |
| Synth. Bulgarian rose oil | 15 |
| Dodecanal 10%* | 10 |
| Eugenol | 10 |
| Synth. orange flower absolute | 10 |
| CEDROXYDE ®⁽¹⁾⁽⁴⁾ | 10 |
| EXALTEX ®⁽⁵⁾ | 10 |
| Galbanum oil 20%* | 5 |
| Total | 920 |

*in diethyl phthalate
⁽¹⁾origin: FIRMENICH SA, Geneva (Switzerland)
⁽²⁾α-methylionone
⁽³⁾hydroxycitronellal
⁽⁴⁾see Swiss Patent No. 474,567
⁽⁵⁾cyclopentadecanolide 8 G of the aldehyde prepared according to the process described in Example 1 were added to 92 g of the above mentioned base composition to give a novel composition whose fragrance was rounder and deeper.

What we claim is:

1. A substantially pure bicyclic aldehyde of formula

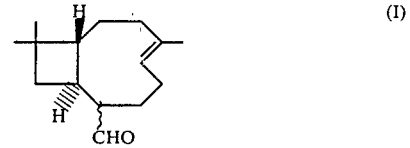

(I)

wherein indicates a C—C single bond of cis or trans configuration with respect to the neighbouring C   H bond.

2. Perfuming composition containing as fragrance active ingredient a bicyclic aldehyde of formula (I) as set forth in claim 1.

* * * * *